United States Patent
Chen et al.

(10) Patent No.: US 9,778,185 B2
(45) Date of Patent: Oct. 3, 2017

(54) ANALYTICAL INSTRUMENT WITH COLLIMATED AND ADJUSTABLE LENGTH OPTICAL PATH

(71) Applicant: Laxco Inc., Bothell, WA (US)

(72) Inventors: Congliang Chen, Bothell, WA (US); Kevin Cassady, Monroe, WA (US)

(73) Assignee: Laxco Incorporated, Bothell, WA (US)

( * ) Notice: Subject to any disclaimer, the term of this patent is extended or adjusted under 35 U.S.C. 154(b) by 0 days.

(21) Appl. No.: 14/923,998

(22) Filed: Oct. 27, 2015

(65) Prior Publication Data

US 2017/0115217 A1    Apr. 27, 2017

(51) Int. Cl.
  *G01N 21/59* (2006.01)
  *G01N 21/27* (2006.01)
  *G01N 21/03* (2006.01)

(52) U.S. Cl.
  CPC ......... *G01N 21/59* (2013.01); *G01N 21/0303* (2013.01); *G01N 21/27* (2013.01);
  (Continued)

(58) Field of Classification Search
  CPC .... G01J 3/0218; G01J 3/02; G01J 3/10; G01J 3/42; G01J 3/0291; G01J 3/00; G01N 21/31; G01N 21/03; G01N 2201/08; G01N 2201/02; G01N 2021/0346; G01N 21/05; G01N 21/255; G01N 21/253; G01N 21/59; G01N 2021/6484
  See application file for complete search history.

(56) References Cited

U.S. PATENT DOCUMENTS 3,740,156 A * 6/1973 Heigl ................ G01N 1/10
                                                250/565
5,739,432 A * 4/1998 Sinha ............... G01N 29/036
                                                73/579

(Continued)

OTHER PUBLICATIONS

"Thermo Scientific NanoDrop Products", retrieved on Oct. 27, 2015 at <<http://www.pragolab.cz/documents/NanoDrop-Products-Brochure.pdf>>, Thermo Fisher Scientific, published 2011.

*Primary Examiner* — Tarifur Chowdhury
*Assistant Examiner* — Mohamed K Amara
(74) *Attorney, Agent, or Firm* — Lee & Hayes, PLLC (57) ABSTRACT

This disclosure relates generally to analytical instruments for measuring one or more properties of specimens or samples to be analyzed and, more particularly, to an analytical instrument with an adjustable optical path length. An analytical instrument may include a specimen support upon which a specimen may rest and a compression plate for controllably adjusting an optical path length of the specimen between the specimen support and the compression plate. In particular, a specimen may contact both the specimen support and the compression plate such that controlling a distance of the compression plate with respect to the specimen support effectively controls the optical path length of the specimen. An analytical instrument may include collimating lenses to collimate electromagnetic energy for transmission through a specimen and converging lenses for directing electromagnetic energy transmitted through the specimen into one or more sensors.

19 Claims, 6 Drawing Sheets

(52) U.S. Cl.
CPC . *G01N 2021/035* (2013.01); *G01N 2021/036* (2013.01); *G01N 2201/0826* (2013.01)

(56) References Cited

U.S. PATENT DOCUMENTS

| | | | | |
|---|---|---|---|---|
| 5,943,122 | A * | 8/1999 | Holmes | G01J 3/02 250/339.07 |
| 6,628,382 | B2 | 9/2003 | Robertson | |
| 6,809,826 | B2 | 10/2004 | Robertson | |
| 7,397,036 | B2 * | 7/2008 | Robertson | G01N 21/645 250/364 |
| 8,189,199 | B2 * | 5/2012 | Robertson, Jr. | G01J 3/02 356/246 |
| 9,170,191 | B2 * | 10/2015 | Coffin | G01N 21/255 |
| 9,606,051 | B2 * | 3/2017 | Kuo | G01N 21/255 |
| 9,625,316 | B2 * | 4/2017 | Zdinak | G01J 3/0291 |
| 2002/0140931 | A1 * | 10/2002 | Robertson | B82Y 15/00 356/246 |
| 2008/0017799 | A1 * | 1/2008 | Sting | G01N 21/0303 250/339.01 |
| 2009/0232448 | A1 * | 9/2009 | Barmash | G02B 6/3504 385/26 |
| 2010/0085571 | A1 * | 4/2010 | Robertson, Jr. | G01N 21/0303 356/432 |
| 2010/0195098 | A1 * | 8/2010 | Zuo | G01N 21/255 356/319 |
| 2015/0233760 | A1 * | 8/2015 | Kielhorn | G01J 3/0218 356/326 |

* cited by examiner

ANALYTICAL INSTRUMENT WITH COLLIMATED AND ADJUSTABLE LENGTH OPTICAL PATH

FIELD OF THE DISCLOSURE

This disclosure relates generally to analytical instruments for measuring one or more properties of specimens or samples to be analyzed and, more particularly, to an analytical instrument with an optical path that is collimated and adjustable in length.

BACKGROUND

Various analytical instruments exist for analyzing properties or characteristics of a material by exposing a specimen or sample of the material to electromagnetic (EM) energy and detecting a response of the specimen or sample to the exposure. For example, light of one or more particular wavelengths and luminous intensities may be emitted into the specimen and an amount of light transmitted through or an amount of light absorbed by the specimen may be measured. As various materials will absorb some wavelengths while reflecting others, various properties of the specimen may be determined by measuring EM energy transmittance and absorbance by the specimen. Furthermore, some materials may exhibit a response known as fluorescence during which the material may actually emit EM energy at a different or shifted wavelength to that which the material is exposed. These spectral responses, among others, may be used to determine properties or characteristics of the material.

The ability to control the optical path length of the specimen may have a considerable effect on the accuracy of analytical results. In particular, the percent of EM energy that is transmitted through a material depends at least partially on the optical path length, e.g. the distance that the EM energy travels through the material. For example, a material may transmit fifty percent of the EM energy of a particular wavelength over an optical path length of 0.2 centimeters (cm) while transmitting only two percent of the EM energy if the optical path length is changed to 1 cm. Therefore, controlling the optical path length is of great importance in obtaining accurate measurements of a material and, resultantly, new approaches to controlling the optical path length while minimizing or eliminating associated EM energy intensity variations, which may lead to improved accuracy in analytical instruments, are desirable.

BRIEF DESCRIPTION OF THE DRAWINGS

The detailed description is described with reference to the accompanying figures. The same reference numbers in different figures indicate similar or identical items.

FIGS. 3A and 3B illustrate cross-section views, taken along cross-section line A-A, of the analytical instrument of claim 1 wherein a cover is in a closed configuration. FIG. 3A illustrates an example compression plate at an upper end of a predefined range of motion while

DETAILED DESCRIPTION

This disclosure provides apparatuses and methods for collimating an optical path and controlling an optical path length of a specimen in order to improve the accuracy of measurements obtained by exposing the specimen to electromagnetic (EM) energy and detecting a response of the specimen to the exposure. It is an object of the present disclosure to enable precise control of an optical path length without the need to tightly control a volume of the specimen under analysis. It is a further object of the present disclosure to enable such control over the optical path length without impacting a luminous intensity of light received at a sensor. It is a further object of the present disclosure to enable highly accurate measurements while using only a small volume of the specimen. Further objects and advantages of the presently disclosed apparatuses and methods are discussed throughout the disclosure.

In various embodiments, an analytical instrument for measuring properties of a test specimen includes a specimen support having a top surface on which a volume of a fluid specimen may be placed, a compression plate having a compression surface with which the fluid specimen may be caused to contact, and an adjustment component for adjustably controlling a position of the compression plate with respect to the specimen support. For example, the fluid specimen may rest on the specimen support in the form of a bead (due to surface tension of the fluid specimen) and then the compression plate may be moved into contact with the bead such that the bead becomes trapped between the top surface of the specimen support and the compression surface of the compression plate. In some embodiments, an electromagnetic (EM) energy source is disposed under the specimen support and an EM energy sensor is disposed above the compression plate. In other embodiments, an EM energy source is disposed above the compression plate and an EM energy sensor is disposed under the specimen support. The EM energy source may emit EM energy, e.g. EM energy extending from infrared to ultraviolet and encompassing visible light, into the fluid specimen and the EM energy sensor may respond to EM energy transmitted through the fluid specimen by producing a signal indicative of at least one property of the fluid specimen. The distance through the fluid specimen that the EM energy travels before reaching the EM energy sensor is referred to herein as the optical path length and is generally equal to a distance between the top surface of the specimen support and the compression surface of the compression plate. The adjustment component may therefore be used to adjustably control the optical path length by changing the position of the compression plate and/or the specimen support with respect to one another. It should be appreciated that although portions of this disclosure may refer to an optical path which generally includes but is not limited to the optical path length as defined herein, the use of the term optical path length specifically refers to the distance that EM energy travels through the specimen (e.g. as illustrated and labeled in FIGS. 5A and 5B).

In some embodiments, an analytical instrument includes a plurality of specimen supports wherein particular specimen supports have a corresponding top surface on which a specimen may be placed, e.g. a bead of the specimen may be placed onto individual specimen supports with a micropipette, and at least one compression plate. For example, once a plurality of beads of one or more specimens have been placed onto particular specimen supports of the plurality of specimen supports, the compression plate may be brought into contact with the plurality of beads thereby forming a plurality of optical paths between particular ones of the top surfaces and at least one compression surface. In various embodiments, the analytical instrument further includes an adjustment component to adjustably control an optical path length of the plurality of optical paths, and a plurality of collimator lenses to collimate EM energy emitted from an EM energy source prior to the EM energy being transmitted through the specimen, and a plurality of converging lenses to direct EM energy transmitted through the specimen into at least one EM energy sensor. Collimating EM energy prior to transmission through the optical path(s) enables modification of the optical path length(s) without changing the intensity of the EM energy due to divergence and/or convergence of the EM energy rays (although the intensity may be affected by the transmittance of the specimen). For example, light sources typically emit non-collimated light such that the rays of light diverge thereby causing luminous intensity of the beam to inversely relate to the distance from the source. Collimating the EM energy prior to transmission through the optical paths improves the accuracy of material property determinations by reducing the effects of luminous intensity drop off as the optical path length is increased.

In some implementations, a method for controlling an optical path length of a fluid specimen includes the steps of placing the fluid specimen onto a specimen support, e.g. in the form of a bead ejected from a pipette, and then bringing a compression plate into contact with the bead. For example, a bead of a fluid may be sandwiched between the specimen support and the compression plate and due to surface tension of the fluid may tend to cling to both a top surface of the specimen support and a compression surface of the compression plate such that an optical path length is formed there between. The method may further include modifying the optical path length by controllably moving the compression plate with respect to the specimen support and causing EM energy of known characteristics to be transmitted through the optical path length of the specimen, measuring an amount of EM energy transmitted through the optical path length of the specimen, and determining one or more properties of the fluid specimen based on the optical path length and the amount of EM energy transmitted through the optical path length of the specimen. In some implementations, the method includes causing one or more actuators, e.g. a high precision linear actuator, to change a position of the compression plate with respect to the specimen support, thereby controlling the optical path length.

It should be appreciated that an amount of EM energy absorbed by the specimen support and the compression plate (and any other optical components for that matter) may be either negligible due to such components being constructed of high transmittance materials and/or may be calibrated out of any measurements. It should also be appreciated that the compression plate does not necessarily exert pressure on any test specimens. In particular, because in many situations the specimen is a fluid, the internal and external pressure of the fluid specimen will typically remain at an equilibrium pressure, e.g. the pressure of the surrounding environment such as atmospheric pressure.

The terms "generally," "substantially," or other terms of degree may be utilized herein to represent the inherent degree of uncertainty that may be attributed to any quantitative comparison, value, measurement, or other representation. One skilled in the art will recognize that in manufacturing any tangible apparatus there may be predetermined tolerance specifications defining the allowable variation from nominal dimensions. For example, a standard for microplate dimensioning numbered ANSI/SLAS 1-2004 published by the American National Standards Institute discloses the acceptable variance from true parallelism certain surfaces may have. The terms are also used herein to represent the degree by which a quantitative representation may vary from a stated reference without resulting in a change in the basic function of the analytical instrument.

Figure 1A:
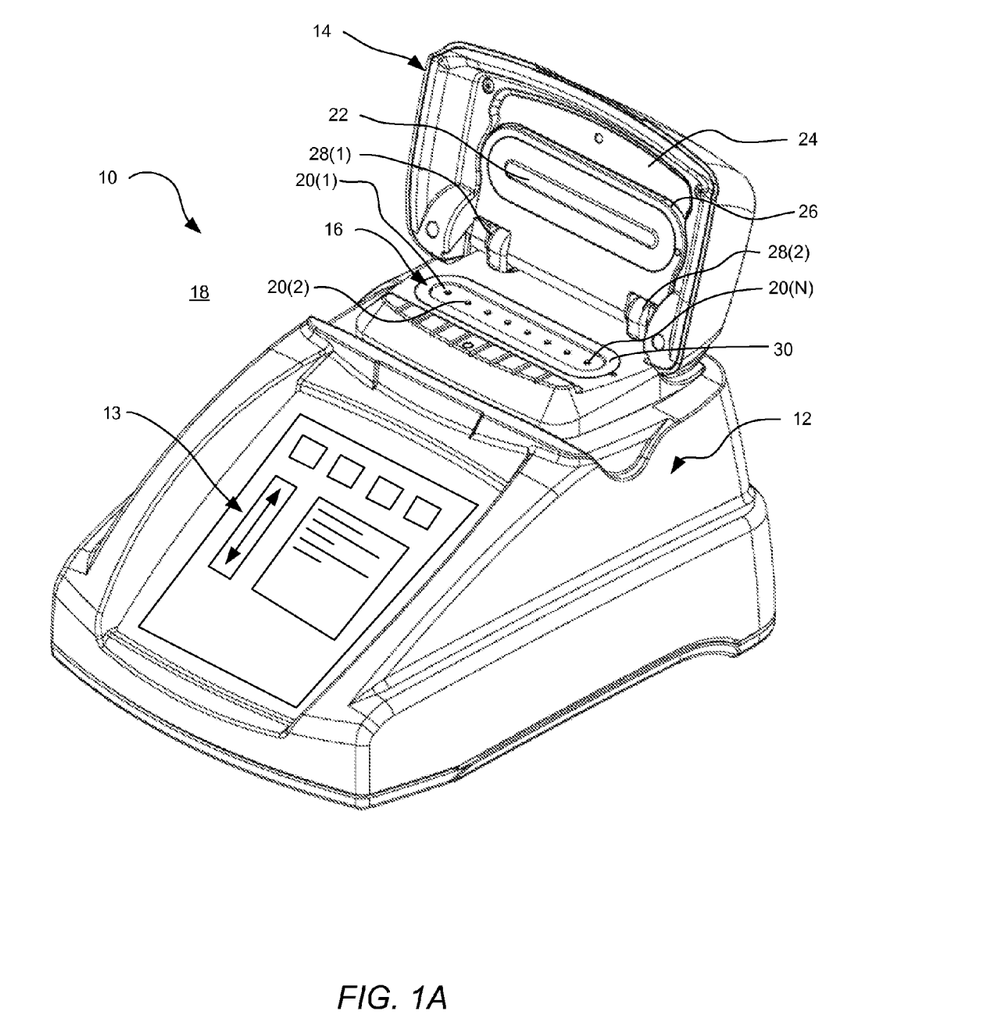
FIG. 1A illustrates an example analytical instrument for measuring specimen properties, wherein a cover is in an open configuration according to one embodiment.
Figure 1B:
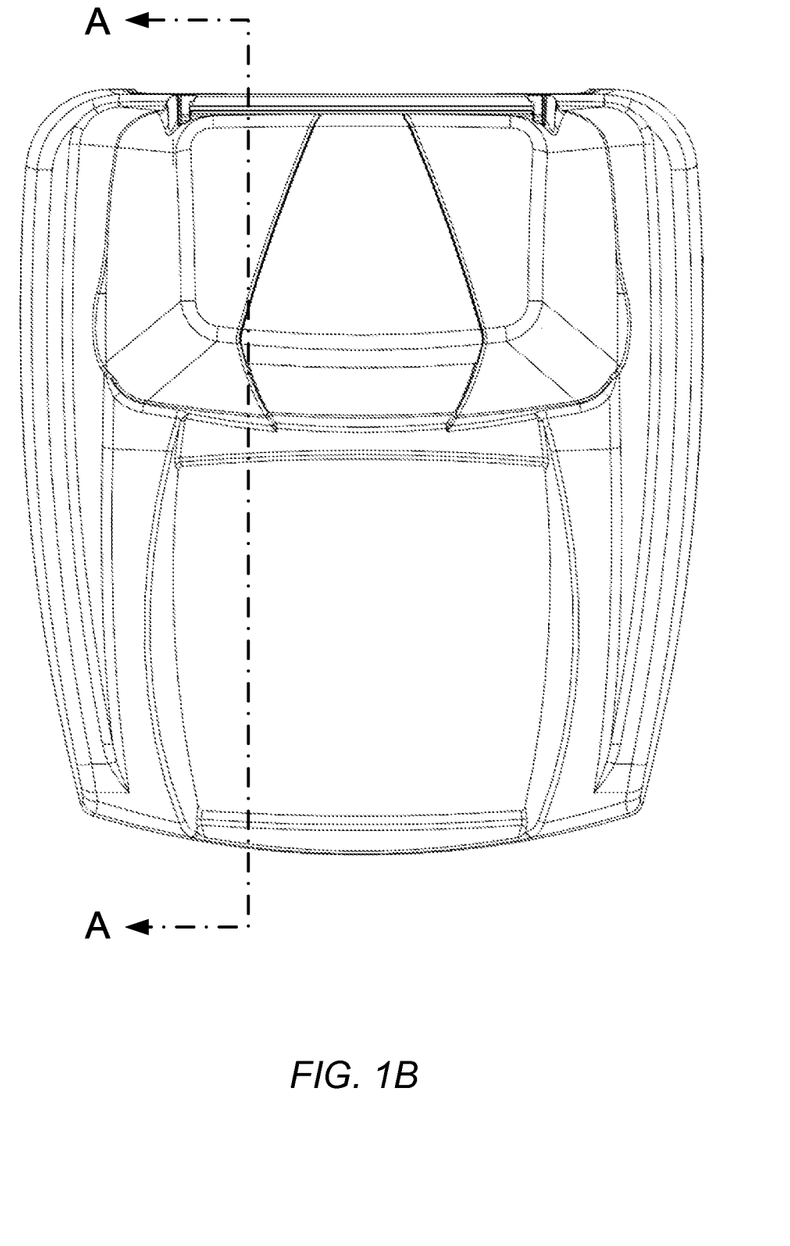
FIG. 1B illustrates a top view of the analytical instrument of claim 1A.

FIGS. 1A & 1B illustrate an analytical instrument 10 for measuring specimen properties according to one embodiment. The analytical instrument 10 may take a variety of forms such as, for example, a spectrometer. In some embodiments, the analytical instrument 10 includes a base 12 and a cover 14 that covers a test area 16. The cover 14 is selectively movable between an open position (illustrated in FIGS. 1 & 2) and a closed position (illustrated in FIGS. 3-5B). For example, the cover 14 may be rotatably coupled to the base 12 allowing the cover 14 to be pivoted between the open and closed positions. The open position or configuration provides access to the test area 16 of the analytical instrument 10 from an exterior thereof 18 allowing for placement of test specimens (not shown in FIG. 1), e.g. one or more fluid test specimens deposited using a micropipette, onto one or more specimen supports 20(1) through 20(N). In some implementations, the test specimens are fluid test specimens having surface tension which holds the test specimens in bead form atop the specimen supports 20. The cover 14 may be moved into the closed position thereby bringing a compression plate 22 into contact with the beads of the fluid test specimen.

In some embodiments, one or more portions of the cover 14 may be configured to be completely static in the closed position while one or more other portions of the cover 14 such as, for example the compression plate 22, may be configured for controlled movement through a predefined range of motion. For example, the cover 14 may include a first support 24, to which various portions of the cover 14 may be affixed to, and a second support 26 to which various other portions of the cover may affixed, including the compression plate 22. In some embodiments, the first support 24 and second support 26 are each rotatably coupled to the base 12 at one or more bearings 28 (labeled 28(1) and 28(2)). In this way, the second support 26 may be moved at least partially independent of the first support 24, e.g. the second support 26 may rotate about the bearings 28 without necessarily causing rotation of the first support 24.

Figure 2:
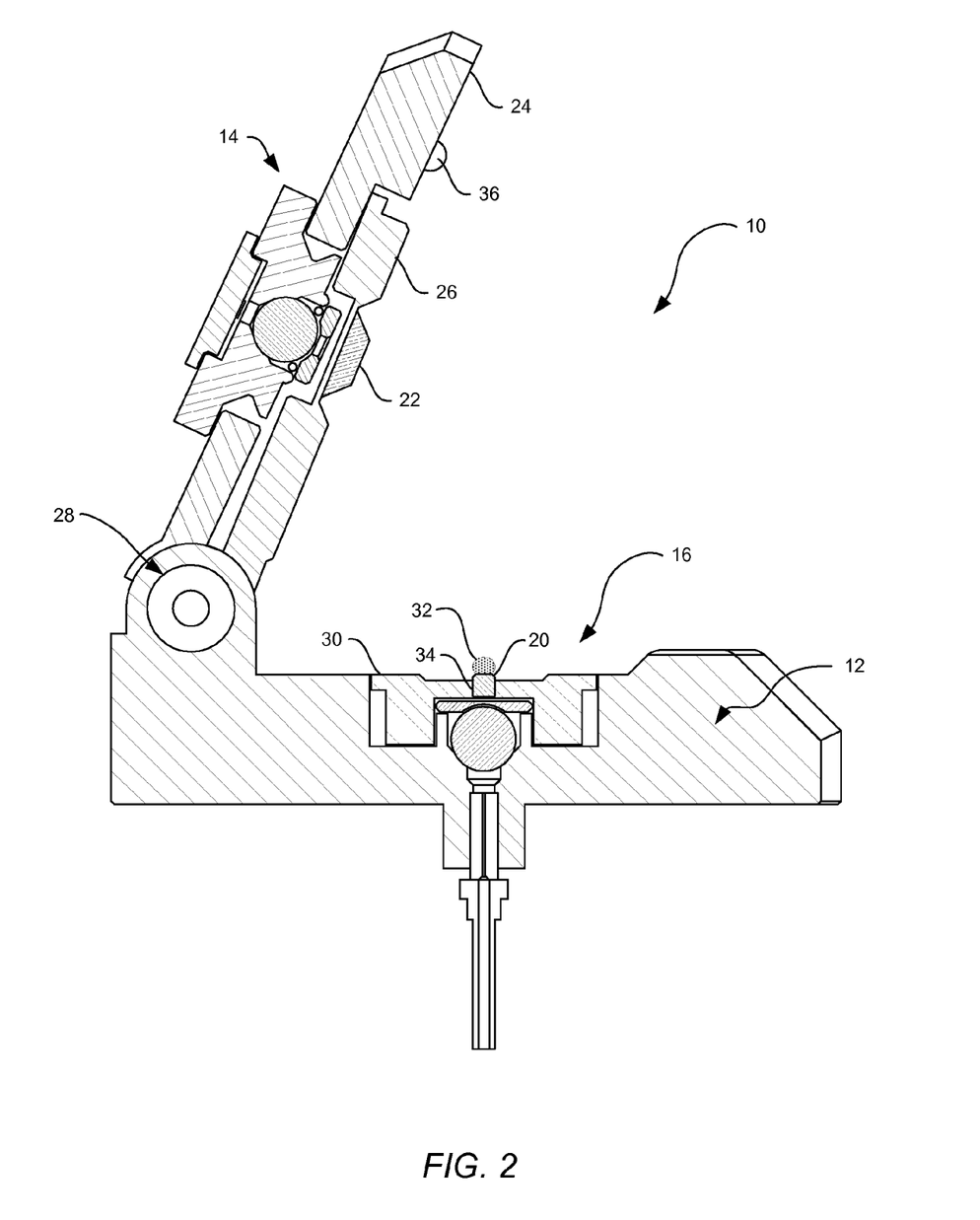
FIG. 2 illustrates a cross-section view of the analytical instrument of FIG. 1, taken along cross-section line A-A which passes through one of a plurality of specimen supports.

FIG. 2 illustrates a cross-section view of the analytical instrument 10 for measuring specimen properties taken through one of the specimen supports 20. It should be appreciated that, for explanatory purposes, FIG. 2 illustrates a simplified depiction of the analytical instrument 10. It should further be appreciated that the analytical instrument 10 is in the open configuration such that the test area 16 is accessible for placement of a test specimen 32 onto the specimen support 20. As illustrated in FIG. 2, the specimen support 20 may include a top surface upon which the test specimen 32 may rest in a bead form due to surface tension of the test specimen 32. As the analytical instrument 10 is in the open configuration, i.e. the first support 24 and second support 26 are rotated away from the base 12 at the bearings 28, the compression plate 22 is not currently in contact with the test specimen 32. With one or more test specimens 32 properly placed within the test area, e.g. a single test specimen 32 atop one or more of specimen supports 20(1)-20(N), the cover 14 (which may include the first support 24 and second support 26) may be moved to the second position as illustrated in FIGS. 3A-3B, thereby bringing the compression plate 22 into contact with the test specimens 32.

In some embodiments, the one or more specimen supports 20 rest atop a test area base plate 30 such that the specimen supports take the form of pedestals as shown in FIGS. 2 through 5B. It should be appreciated that such embodiments may assist a user in accurately placing a test specimen at the correct locations within the analytical instrument 10. In particular, in taking a spectrometer measurement, the test specimen should typically be properly aligned within an optical system or train. Accordingly, embodiments wherein the specimen supports 20 are in pedestal form provide a user with a visual target for placement of the test specimens as well as visual confirmation that the test specimens are properly aligned, e.g. either resting atop or wholly covering the specimen support. Furthermore, in some embodiments, the specimen support 20 rests within a well 34 of the test area base plate 30. The well 34 may ensure accurate placement of the specimen support 20 within an optical system.

Figure 3A:
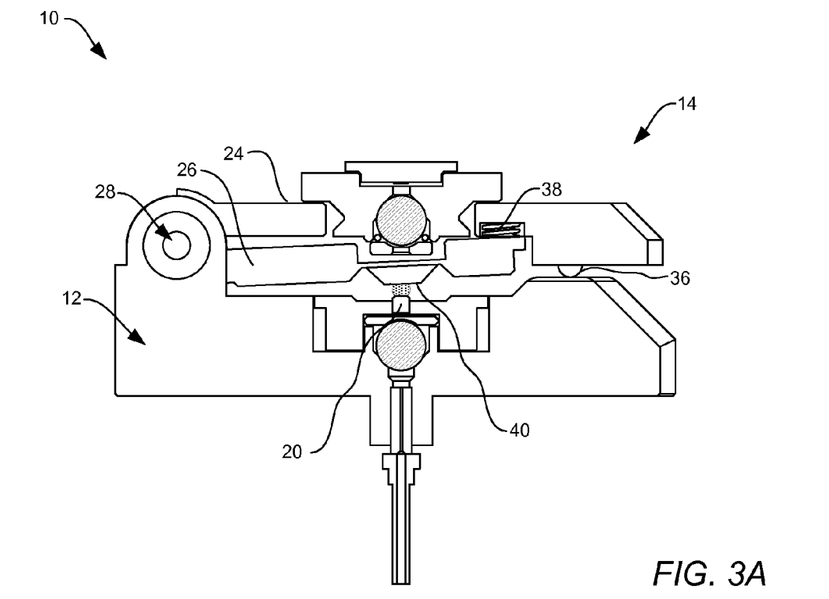
Figure 3B:
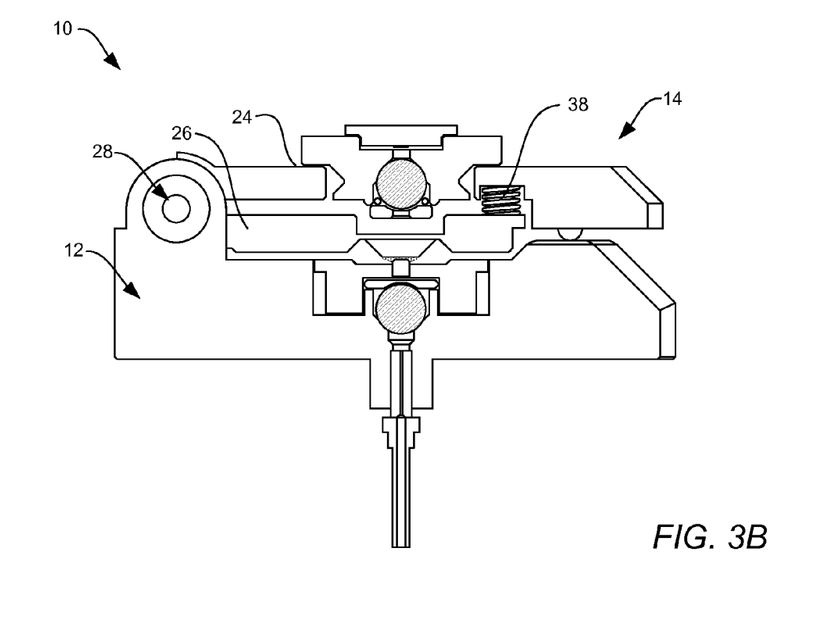
FIG. 3B illustrates the compression plate at a lower end of the predefined range of motion.

With particular reference to FIGS. 3A & 3B, in some embodiments one or more portions of the cover 14 may be configured to remain static while the cover 14 is in the closed configuration, whereas one or more other portions of the cover 14 may be configured to dynamically move through a predefined range of motion while the cover 14 is within the closed position. For example, in the illustrated embodiment, the cover 14 includes both the first support 24 and the second support 26 which are both rotatably coupled to the base 12 at the bearings 28. In some embodiments, the first support 24 includes one or more positive stops 36 which physically contact at least a portion of the base 12 in the closed position to ensure the first support 24 of the cover 14 remains static while in the closed position. In some embodiments, the one or more positive stops 36 may be magnetically attracted to the one or more portions of the base 12 in order to more fully ensure the proper closed position is both achieved and maintained. The one or more positive stops 36 may also protrude from the first support 24 to reduce the likelihood of loose debris being located within an area of contact between the base 12 and the positive stops 36.

Figure 4A:
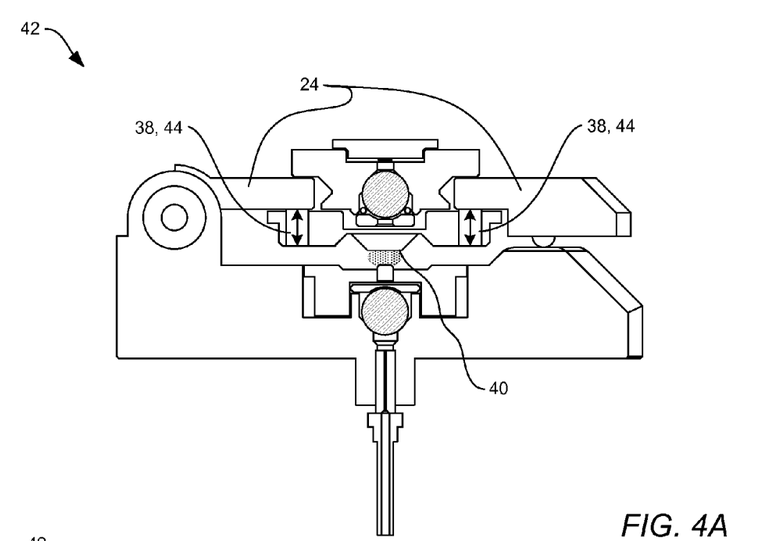
FIGS. 4A and 4B illustrate cross-section views of an example analytical instrument in accordance with another embodiment wherein a compression plate remains substantially perpendicular to an optical path throughout a predefined range of motion.
Figure 4B:
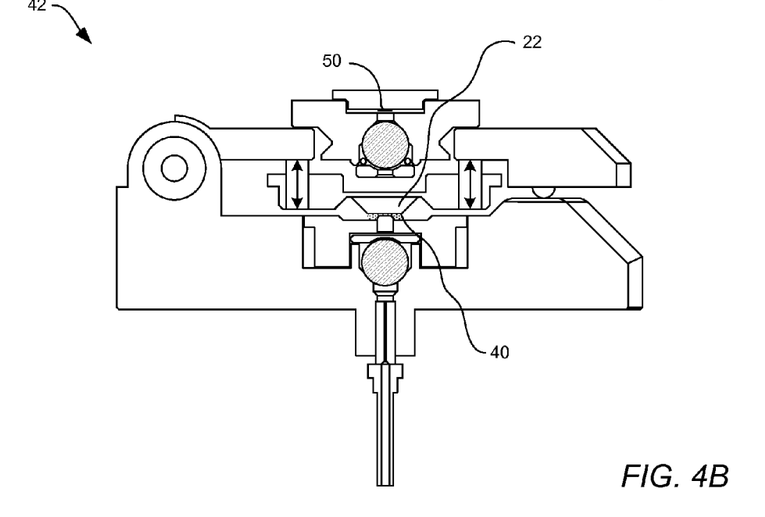

In some embodiments, the analytical instrument 10 may include an adjustment component 38 that is operable to adjustably control a position of the second support 26 with respect to the first support 24. For example, between FIGS. 3A and 3B the second support 26 has been moved downward with respect to the first support 24 and, therefore, the base 12 and specimen support 20. In the embodiment illustrated in FIGS. 3A & 3B, the second support 26 is coupled to the base 12 at the bearing 28 and also coupled to the first support 24 at the adjustment component 38 such that operating the adjustment component 38 causes the second support 26 to pivot at the bearing(s) 28. It should be appreciated that in the illustrated embodiment, a compression surface 40 of the compression plate 22 does not remain parallel to the top surface of the specimen support 20 throughout the entire predefined range of motion of the second support 26 within the closed configuration. In other embodiments, the compression surface 40 may be configured to remain substantially parallel to the top surface of the specimen support 20 even when the adjustment component 38 is operated to move the compression plate 22 with respect to other component of the analytical instrument. For example, FIGS. 4A and 4B illustrate an analytical instrument 42 in accordance with an embodiment which is configured to maintain the compression surface 40 in a substantially parallel relationship to the top surface of the specimen support 20 as the compression plate 22 is moved with respect to other components of the analytical instrument 42 in the closed configuration. As illustrated, the analytical instrument 42 may be configured such that the first support 24 is rotatably coupled to the base 12 at the bearing(s) 28, whereas the second support 26 (to which the compression plate is affixed) is only indirectly coupled to the base 12 through the first support 24. In particular, the second support 26 may be coupled to the first support 24 by the adjustment component 38 but not rotatably coupled to the base 12. It should be appreciated that cross-hatching may be omitted from one or more component cross-sections for clarity of the illustrations.

In some embodiments, the adjustment component 38 may be configured for substantially linear adjustment throughout the predefined range of motion. For example, the adjustment component 38 may not be limited to preset adjustment increments, e.g. may not be limited to enabling only adjustments to any one of a set of preset adjustment increments. The adjustment component 38 may include one or more miniature linear position actuators which may be controlled via user input at the user interface 13 (See FIG. 1). For example, the one or more miniature linear position actuators may be in communication with one or more computing devices which may receive an input via the user interface 13 which includes an instruction to move the compression plate 22, via operation of the actuators, into a specified position. In some embodiments, the analytical instrument 42 may further include one or more linear position sensors 44 which may or may not be integrated into the adjustment component 38. The one or more linear position sensors 44 may be in communication with the one or more computing devices to output an indication of the position of the compression plate 22. For example, the user interface 13 may display an optical path length of the test specimen 32, e.g. a distance between the compression surface 40 and the top surface of the specimen support 20. In some embodiments, the adjustment component 38 may be configured for manual adjustment such as, for example, through an operator turning one or both of a course adjustment dial and/or a fine adjustment dial to achieve a desired optical path length. Furthermore, the one or more linear position sensors 44 may be configured to output the optical path length in real time (e.g. without perceptible delay) thereby assisting an operator with achieving the desired optical path length through manual adjustment. In some embodiments, the adjustment component 38 may include at least one of a coarse adjustment dial or a fine adjustment dial. In some embodiments, the adjustment component 38 may also include a mechanical biasing mechanism such as a spring (depicted in FIGS. 3A and 3B) to secure a position of the second support with respect to the first support, e.g. removing play associated mechanical adjustment dials.

In some embodiments, the adjustment component 38 may be configured for incremental adjustment throughout the predefined range of motion. In particular, the adjustment component 38 may enable adjustment to any one of a set of preset adjustment increments such as, for example, 10 microns (g) increments throughout a predefined range of motion of 1250μ.

Figure 5A:
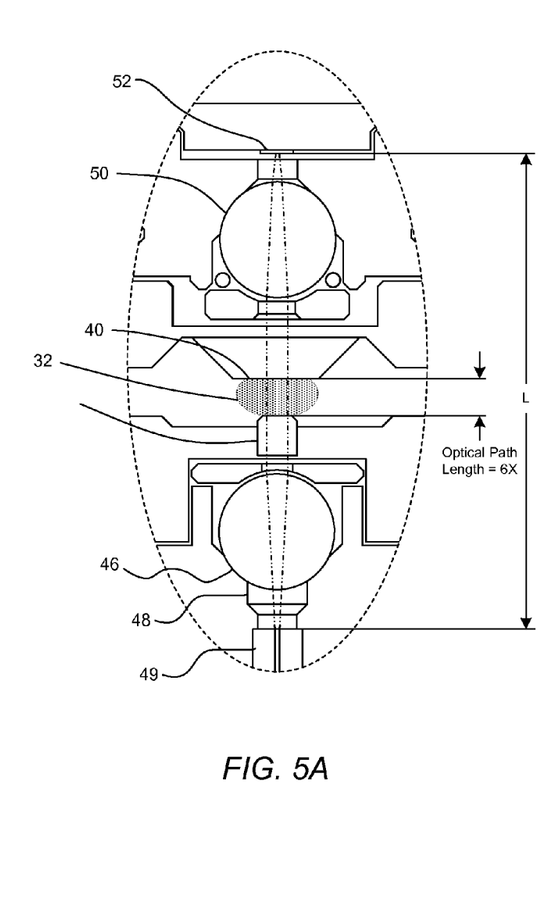
FIGS. 5A and 5B illustrate a region of the analytical instrument of FIGS. 4A and 4B defining an optical path between an EM energy source, such as a light emitting diode, and an EM energy sensor, such as a charge-coupled device (CCD) sensor.
Figure 5B:
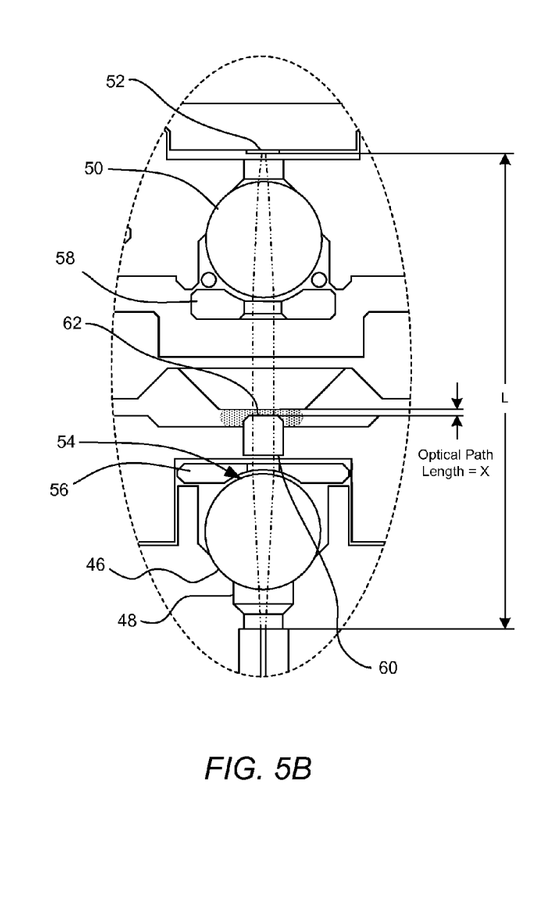

FIGS. 5A and 5B illustrate a region of the analytical instrument 42 of FIGS. 4A and 4B defining an optical path between an EM energy source 48, such as a light emitting diode (LED), and an EM energy sensor 52, such as a CCD sensor. Preferably, the EM energy sensor 52 is either a charge-coupled device (CCD) or an active-pixel sensor (APS) such as, for example, a complementary metal-oxide-semiconductor (CMOS) sensor. As illustrated, some embodiments of the analytical instrument 42 may include one or more collimating lenses 46 disposed between the specimen support 20 and the EM energy source 48 and/or one or more converging lenses 50 disposed between the compression plate 22 and the EM energy sensor 52. It should be appreciated that the analytical instrument 10 may include multiple such optical paths as depicted in FIGS. 5A and 5B. For example, one such optical path may correspond to each of specimen supports 20(1)-20(N) (as shown in FIG. 1). In a preferred embodiment, the analytical instrument 42 may include eight such optical paths each of which include a corresponding specimen support.

In the illustrated embodiment, the optical path begins at the EM energy source 48 which emits EM energy such as, for example, visible light which is then transmitted through the collimating lens 46. The EM energy source 48 may include a fiber optic cable 49 which transmits EM energy from an original source such as an LED located elsewhere within the analytical instrument 42. In some embodiments, the collimating lens 46 is a ball lens as illustrated which has advantages associated with manufacturing. In particular, the use of a ball lens may eliminate the need for precise orientation of the collimating lens and/or converging lens 46 with respect to other components such as the EM energy source 48 or specimen support 20. As EM energy passes through an upper boundary 54 of the collimating lens 46 the EM energy is refracted such that it becomes substantially collimated throughout the optical path until reaching the converging lens 50. Although the collimating lens and converging lens are both depicted as ball type lenses, it should be appreciated that other types of lenses may be used without departing from the scope of the present disclosure.

In some embodiments, the analytical instrument 42 may be configured such that each boundary between optical components located between the collimating lens 46 and the converging lens 50 is perpendicular to the direction of the collimated light path thereby eliminating refraction at each boundary. For example, with reference to FIG. 5B, light emitted from the EM energy source 48 becomes collimated as it passes through the upper boundary 54 and source aperture 56. Then, the light enters the specimen support 20 at a bottom surface 60 and exits the specimen support at a top surface 62 which is also a boundary between the specimen support 20 and the test specimen 32. Then, the light enters the compression plate 22 at the compression surface 40 prior to ultimately passing through the receiving aperture 58 and the diverging lens 50 before being received at the EM energy sensor 52. As shown in FIG. 5B, each boundary between the collimating lens 46 and the diverging lens 50 is parallel to the collimated light path. In other embodiments, the analytical instrument 10 may be configured that any deviation from perpendicularity of the collimated light path with respect to each boundary is negligible and/or calibrated or calculated out. For example, with particular reference to FIG. 3A the boundary between the compression plate 22 and the test specimen 32, as defined by the compression surface 40, is not parallel to the collimated light path (not shown). Accordingly, EM energy passing through the medium boundary created by the compression surface 40 may be refracted. Preferably, the analytical instrument 10 is configured such that any amount of refraction at the various boundaries and, in particular, at the boundary of the compression surface is negligible.

In some embodiments, the analytical instrument further includes a source aperture 56 and a receiving aperture 58 each for eliminating EM energy from the system other than that emitted by the EM energy source 48. For example, the source aperture 56 and receiving aperture 58 may each be made of an opaque material and may each include a small hole slightly larger in diameter than the light path as outlined by dashed lines extending from the EM energy source 48 to the EM energy sensor 52.

The analytical instrument disclosed herein has the distinct advantage of enabling precise and linear adjustment of an optical path length without impact to the intensity of the EM energy due to such adjustment. In particular, by collimating the EM energy prior to transmission through the test specimen 32 any effect on the intensity due to divergence of the EM energy rays (as depicted prior to transmission through the upper boundary 54 of the collimating lens 46) is effectively reduced or eliminated. For example, the intensity of the EM energy passing through the compression surface 40 in FIG. 5A neither increases nor decreases due to the optical path length being reduced in length from 6X to X. It should be appreciated, however, that the intensity of the EM energy passing through the compression surface 40 may change due to other factors such as an increase in absorption by the test specimen 32 as the optical path length increases as modelled by Beer's Law.

In some embodiments, an overall length L (labelled in FIGS. 5A and 5B) of the entire optical path between the EM energy source 48 and the EM energy sensor 52 does not change as the optical path length (i.e. the adjustable length depicted in FIGS. 5A and 5B) is adjusted. In other embodiments, the overall length does change as the optical path length is adjusted.

In some embodiments, the EM energy sensor 52 includes a receiving area that is larger than a corresponding area of the EM energy received by the EM energy sensor. For example, with reference to FIG. 5A it should be appreciated that the EM energy sensor 52 is larger than the path of the incoming EM energy (the boundary of which is outlined in dashed lines). Such embodiments may ensure that substantially all of the light that is not absorbed by the test specimen is received at the EM energy sensor 52.

In various embodiments, particular optical components such as, for example, the collimating lens 46, the specimen support 20, the compression plate 22, and the converging lens 50 may be made of sapphire, glass, plastic, ultraviolet quartz, or any another suitable material for use with the intended wavelength of light. In a preferred embodiment, any components which may be inadvertently physically contacted during normal operation or maintenance are constructed of a corresponding single piece of sapphire due to the material being highly scratch resistant. For example, during normal operation the specimen support 20 may be inadvertently contacted by the tip of a micropipette as a specimen bead is placed.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

What is claimed is:

1. An analytical instrument for measuring at least one property of a specimen, the analytical instrument comprising:
   a specimen support having a top surface and a bottom surface, the specimen support being affixed to a base;
   a first support coupled to the base;
   a compression plate supported by the first support and having a compression surface, wherein the compression plate is non-contiguous with the specimen support such that an optical path length is defined between the top surface and the compression surface when the compression surface is in a closed position;
   an adjustment component on the first support and at least partially coupling the compression plate to the first support, the adjustment component operable to linearly control a position of the compression plate with respect to the specimen support thereby adjustably controlling the optical path length, wherein the adjustment component operates independently of the position of the first support;
   an electromagnetic (EM) energy source disposed under the bottom surface, the EM energy source operable to transmit EM energy through the specimen while the specimen is in contact with each of the top surface of the specimen support and the compression surface of the compression plate;
   a collimator lens disposed between the EM energy source and the specimen support to collimate the EM energy emitted by the EM energy source prior to transmission of at least a portion of the EM energy through the specimen;
   an EM energy sensor disposed above the compression plate and opposite the compression surface, the EM energy sensor responsive to EM energy received at the EM energy sensor to produce a signal indicative of the at least one property of the specimen; and
   wherein the first support is rotatably coupled to the base and is rotatable between an open position, at which the specimen support is exposed, and the closed position, at which the specimen support is substantially covered by at least the compression plate.

2. The analytical instrument of claim 1, wherein the first support at least partially supports the adjustment component and the EM energy sensor.

3. The analytical instrument of claim 1, further comprising:
   a first support that at least partially supports the EM energy sensor and the adjustment component; and
   a second support that at least partially supports the compression plate and is coupled to the first support through the adjustment component, the adjustment component being operable to control a position of the second support with respect to the first support thereby adjustably controlling the optical path length.

4. The analytical instrument of claim 3, wherein each of the first support and second support are coupled to the base and rotatable between an open position and a closed position.

5. The analytical instrument of claim 1, wherein the adjustment component includes a linear position actuator operable to linearly adjust the optical path length.

6. The analytical instrument of claim 5, further comprising a linear position sensor operable to determine the position of the compression plate with respect to the specimen support and produce a signal indicative of the optical path length.

7. The analytical instrument of claim 1, further comprising a converging lens disposed between the compression plate and the EM energy sensor to direct EM energy received after transmission through the specimen into the EM energy sensor.

8. The analytical instrument of claim 7, wherein each of the collimator lens and the converging lens are comprised of a respective ball lens.

9. The analytical instrument of claim 1, wherein the EM energy sensor comprises at least one of a charge-coupled device or an active-pixel sensor.

10. An analytical instrument, comprising:
    a plurality of specimen supports affixed to a base, particular specimen supports of the plurality of specimen supports having a corresponding top surface and a corresponding bottom surface such that the plurality of specimen supports includes a plurality of top surfaces and a plurality of bottom surfaces;
    a first support coupled to the base;
    at least one compression plate having at least one compression surface, the at least one compression surface being attached to the first support and spaced a distance from at least some of the plurality of top surfaces thereby defining a plurality of optical paths;
    an adjustment component coupled to the first support and operable to adjustably control, by linearly moving the at least one compression plate with respect to the plurality of specimen supports independently of a position of the first support, at least one optical path length of the plurality of optical paths;
    a plurality of first optical fibers, particular ones of the plurality of first optical fibers being disposed between particular ones of the plurality of bottom surfaces and at least one electromagnetic (EM) energy source, the at least one EM energy source operable to emit EM energy through a specimen while the specimen is in contact with at least one of the plurality of top surfaces and the at least one compression surface;
    a plurality of collimator lenses to collimate the EM energy prior to transmission through the specimen, particular ones of the plurality of collimator lenses being disposed between particular ones of the plurality of first optical fibers and the at least one EM energy source; and
    a plurality of converging lenses to direct the EM energy into at least one EM energy sensor, the at least one EM energy sensor responsive to the EM energy transmitted through the specimen to produce a signal indicative of at least one property of the specimen,
    wherein the first support is rotatably coupled to the base and is rotatable between an open position, at which the specimen support is exposed, and the closed position, at which the specimen support is substantially covered by at least the compression plate.

11. The analytical instrument of claim 10, further comprising:
    a second support that is rotatably coupled to the base and at least partially coupled to the first support through the adjustment component, the second support being coupled with the at least one compression plate, wherein the first support and the second support are jointly rotatable between an open position, at which the plurality of specimen supports are exposed, and a closed position, at which the first support is configured to remain static while the second support is configured to be dynamically adjustable through operation of the adjustment component.

12. The analytical instrument of claim 10, wherein the first support is coupled with the plurality of converging lenses and the at least one EM energy sensor; and further comprising
a second support that is coupled to the first support through the adjustment component, the second support being coupled with the at least one compression plate, wherein the at least one compression surface remains substantially parallel to the plurality of top surfaces during operation of the adjustment component.

13. The analytical instrument of claim 10, further comprising a test area base plate disposed at least partially between the plurality of collimator lenses and the plurality of specimen supports, wherein particular ones of the plurality of specimen supports protrude from the test area base plate such that the plurality of top surfaces form a plurality of specimen pedestals, each for receiving a liquid bead of the specimen.

14. The analytical instrument of claim 13, wherein the test area base plate comprises a plurality of wells, particular ones of the plurality of wells configured to receive a corresponding specimen support of the plurality of specimen supports.

15. The analytical instrument of claim 10, further comprising at least one linear position sensor operable to produce a signal indicative of the at least one optical path length of the plurality of optical paths.

16. The analytical instrument of claim 10, further comprising:
a plurality of source apertures, particular ones of the plurality of source apertures being disposed between particular ones of the plurality of collimator lenses and particular ones of the plurality of specimen supports; and
a plurality of receiving apertures, particular ones of the plurality of receiving apertures being disposed between particular ones of the plurality of converging lenses and the at least one compression plate.

17. The analytical instrument of claim 10, wherein the adjustment component comprises an actuator operable to linearly adjust the at least one optical path length.

18. The analytical instrument of claim 10, wherein the at least one EM energy sensor includes a receiving area that is larger than a cross-sectional area of the EM energy adjacent to the receiving area such that substantially all of the EM energy transmitted through the plurality of converging lenses is directed into the at least one EM energy sensor.

19. The analytical instrument of claim 10, wherein the at least one EM energy sensor comprises at least one of a charge-coupled device or an active-pixel sensor.

* * * * *